United States Patent [19]

Namba et al.

[11] Patent Number: 4,743,544

[45] Date of Patent: May 10, 1988

[54] METHOD FOR MEASURING SUBSTANCES BY ENZYME IMMUNOASSAY

[75] Inventors: Yuzaburo Namba, Saitama; Tohru Naraki; Takashi Sawada, both of Gifu; Toyohiro Kitamura, Chiba; Minoru Tohda, Gifu; Tomiaki Morimoto, Tokyo, all of Japan

[73] Assignee: Eisai Co., Ltd., Tokyo, Japan

[21] Appl. No.: 609,530

[22] Filed: May 14, 1984

Related U.S. Application Data

[63] Continuation of Ser. No. 349,255, Feb. 16, 1982, abandoned.

[30] Foreign Application Priority Data

Feb. 18, 1981 [JP] Japan ................... 56-21366

[51] Int. Cl.$^4$ ............... G01N 33/53; G01N 33/566; G01N 33/543
[52] U.S. Cl. ...................... 435/7; 436/501; 436/518
[58] Field of Search ............. 435/4, 7, 291, 810; 422/68, 81, 99; 436/501, 518

[56] References Cited

U.S. PATENT DOCUMENTS

| | | | |
|---|---|---|---|
| Re. 30,562 | 3/1981 | Park | 435/7 |
| Re. 31,006 | 8/1982 | Schuurs et al. | 435/810 X |
| 4,154,795 | 5/1979 | Thorne | 422/99 |
| 4,234,680 | 11/1980 | Hevey et al. | 435/7 |
| 4,246,339 | 1/1981 | Cole et al. | 435/7 |
| 4,254,223 | 3/1981 | Schuurs et al. | 435/7 |
| 4,341,866 | 7/1982 | Yoshida | 435/7 |

OTHER PUBLICATIONS

Maggio, E. T. *Enzyme-Immunoassay*, CRC Press, Inc., Fla., 1980, pp. 16-18.

Primary Examiner—Charles F. Warren
Assistant Examiner—Jeremy M. Jay
Attorney, Agent, or Firm—Wenderoth, Lind & Ponack

[57] ABSTRACT

Improved method for the measurement of substance comprising simultaneously measuring a plurality of specimens of a substance to be measured by enzyme immunoassay. The process comprises:

a. reacting specimens and a material which will be specifically combined with the substance to be measured and which has been made in the solid phase;
b. separating the reaction mixture in step (a) into the solid phase and the liquid phase;
c. reacting the solid phase with an enzyme-labelled product of a material which will be specifically combined with the substance to be measured;
d. separating the reaction mixture in the step (c) into the solid phase and the liquid phase;
e. reacting the solid phase or the liquid phase with a substrate for the enzyme in the step (c); and
f. measuring the optical density of the reaction mixture. The improvement comprises, in step (a), successively contacting the respective specimens with the material which will be specifically combined with the substance to be measured and which has been made in the solid phase, under cooling condition at a temperature ranging from 0° C. to 15° C., followed by simultaneously incubating them at a temperature ranging from room temperature to 45° C. The fluctuation of results can be remarkably smaller by the employment of cooling means.

3 Claims, 2 Drawing Sheets

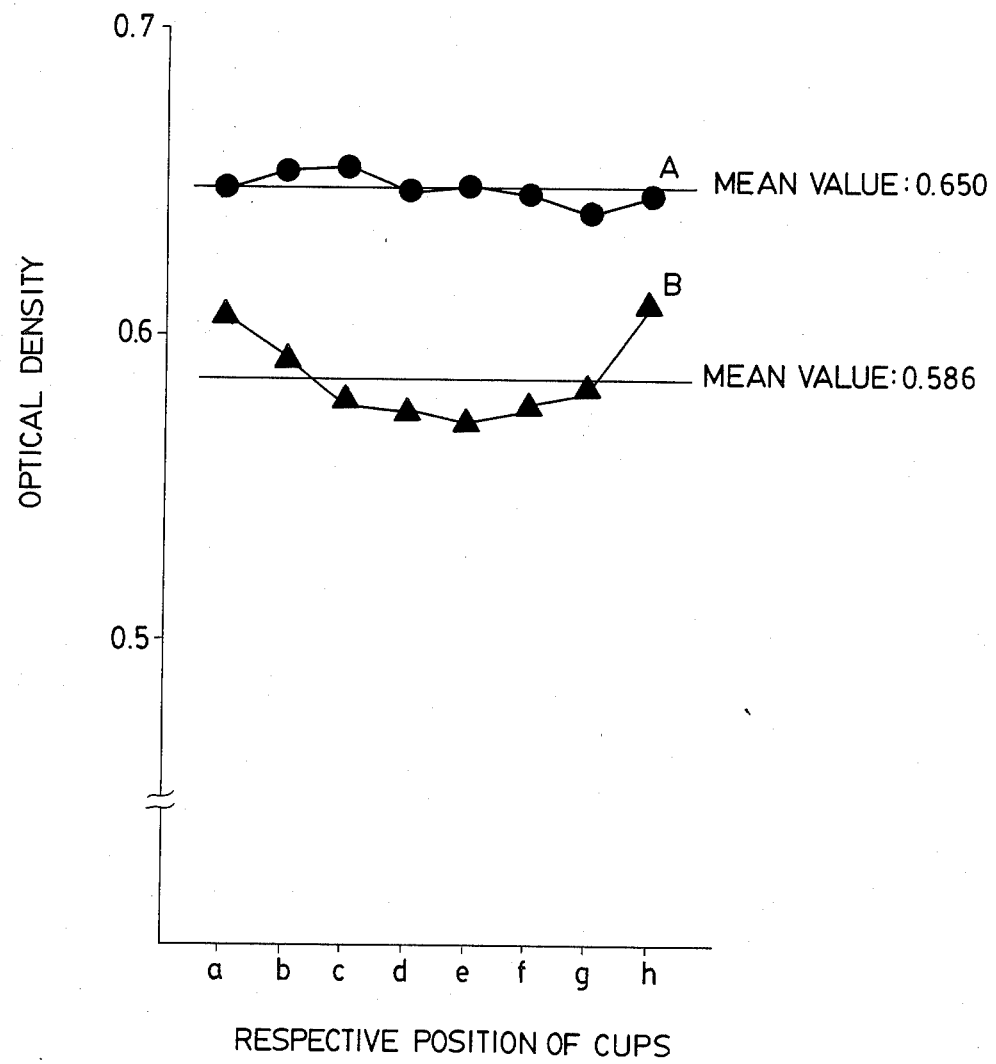

METHOD FOR MEASURING SUBSTANCES BY ENZYME IMMUNOASSAY

This application is a continuation of now abandoned application Ser. No. 349,255, filed Feb. 16, 1982, now abandoned.

BACKGROUND OF THE INVENTION

This invention relates to an improvement in the sandwich method for enzyme immunoassay.

The sandwich method of enzyme immunoassay is an excellent method which has been lately developed as a microassay of substances, as disclosed in Japanese Patent Publication No. 47011/1977, Japanese Patent Application Laid-open Nos. 32114/1977 and 57316/1977, "Igaku no Ayumi (Progress of Medicine)", vol. 102, No. 2, pages 57–65, and the like. This is being employed mainly for measuring antigenic substances, such as α-fetoprotein, HBs antigens, hormones etc.

On measuring a substance using this sandwich method enzyme immunoassay, while it is possible to separately conduct measurements on the respective specimens, it is more common to conduct measurements collectively on a plurality of specimens in which the same substance is to be detected. When measuring collectively, the plurality of specimens are successively contacted at room temperature with a material which will be specifically combined with the substance to be measured and which has been made in the solid phase, after which they are reacted at a temperature ranging from room temperature to 45° C. and subjected to the subsequent steps to complete the measurement. However, in this case, there is a disadvantage wherein a great fluctuation occurs in the results. This is the reason why, since the plurality of specimens is successively contacted with the material which will be specifically combined with the substance to be measured and which has been made in the solid phase, there is a considerable time lag between the specimen contacted first and the specimen contacted last. Such a time lag is the greatest in the above step, although some lag in time is also inevitably produced in the subsequent steps. It is believed that the fluctuation of results is due to this time lag. Therefore, the greater the number of the speciments to be measured at one time, the greater the fluctuation.

SUMMARY OF THE INVENTION

The method of this invention relates to an improvement for eliminating the above-described disadvantage. More particularly, this invention is characterized by the employment of cooling means, resulting in that the fluctuation of results can be minimized.

Accordingly, this invention provides a method for measuring a substance, characterized by simultaneously measuring a plurality of specimens by enzyme immunoassay which comprises the steps of:

a. reacting a substance to be measured (specimens) with a material which will be specifically combined with the substance to be measured and which has been made in the form of a solid phase;

b. separating the reaction mixture in the step (a) into the solid phase and the liquid phase;

c. reacting the solid phase with an enzyme-labelled product of a material which will be specifically combined with the substance to be measured;

d. separating the reaction mixture in the step (c) into the solid phase and the liquid phase;

e. reacting the solid phase or the liquid phase with a substrate for the enzyme in the step (c); and f. measuring the optical density of the reaction mixture; in the step (a), successively contacting the respective specimens with the material which will be specifically combined with the substance to be measured and which has been made in the solid phase, under cooling condition at a temperature ranging from 0° C. to 15° C., followed by simultaneously incubating them at a temperature ranging from room temperature to 45° C.

DETAILED DESCRIPTION OF THE INVENTION

Subsequent to the above step (a), the above-described steps (b)–(f) are conducted in conventional manner to measure the substance in the specimens.

The reaction of the above step (a) is effected either by reacting the material which has been made in the solid phase with the specimen in a reactor, e.g. a test tube etc. which has been previously arranged, or by adding the specimen to the material which has been made in the solid phase and also serves as a reactor itself, e.g., a microtiter plate or cup, etc., (that is, the material which will be specifically combined with the substance to be measured is coated on or fixed to the inner wall of the reactor), to induce the reaction. In this reaction, in order to control the temperatures ranging from 0° C. to 15° C. and also ranging from room temperature to 45° C., there may be used ice, cold water or an electric cooling device, such as a cooling plate etc., as the cooling means and hot water bath, an incubator or a hot plate as the heating means, for such temperature control.

The step b may be conducted by removing the reacted solution and washing the solid phase with water, buffer, etc.

The step (c) may be conducted by reacting the solid phase with the enzyme-labelled product of the material which will be specifically combined with the substance to be measured, at a temperature ranging from room temperature to 45° C. Also in this step, on successively adding the enzyme-labelled product to the solid phase, it is desirable to add it at a temperature ranging from 0° C. to 15° C. and conduct the reaction at a temperature ranging from room temperature to 45° C. in order to minimize the fluctuation of results.

In the step (d), the reacted solution and the solid phase are separated from each other. Where the solid phase is used in the subsequent step (e), the separated solid phase is washed with buffer, water etc.

The step (e) may be effected by successively adding a solution of a substrate for the enzyme used to each solid phase or liquid phase obtained in the step (d), so as to carry out the enzyme reaction, followed by adding, after a certain time, a stopping solution for the enzyme reaction to the final reaction mixture. The temperature for the above enzyme reaction is adjusted to the optimum temperature for the enzyme used. Also in this step, on adding the substrate solution to the solid phase or the liquid phase, and on adding the reaction stopping solution to the reaction mixture, it is desirable to conduct this operation at a temperature ranging from 0° C. to 15° C., in order to minimize the fluctuation of results.

The step (f) may be conducted by measuring the optical density of the substrate decomposed liquor on a spectrophotometer using the wavelength suitable for the quantitative assay thereof.

In the above measuring system, the optical density is measured beforehand using a set of known amounts of the substance and the calibration curve is obtained between their amounts and optical densities. Thereafter, on the specimen of the unknown amount, the optical density is measured using the same measuring system, whereby the amount of the substance to be measured in the specimen is determined from the above calibration curve.

In this invention, in order to minimize the fluctuation of results, as described above, in the step (a), and preferably also in the steps (c) and (e), the reactants are added under cooling condition at a temperature ranging from 0° C. to 15° C. Further, in the steps (b) and (d), where the separation of the solid phase and the liquid phase is successively conducted on each specimen, these steps are also desirably conducted under cooling condition at a temperature ranging from 0° C. to 15° C.

In this invention, on cooling or heating, the temperature control is easily effected by using a metal holder with which the outer wall of the reactor is colsely contacted. For instance, a plate made of a good thermoconductor such as aluminum, copper, iron etc., is provided with a predetermined number of holes so that reactors can be inserted thereinto in close contact therewith, or that having such a shape is made by casting, the reactors are inserted into such holes, and the temperature is controlled by the above-described cooling or heating means. In addition to the above shape, there may be mentioned a shape which has cylindrical protrusion so as to insert the reactor into the cylinder, or a shape wherein the outer wall of the reactor is covered with a metal foil or a metal plate. These may be constructed in such shape that the reactors are installable or removable, or the reactors are unified.

By employing such devices, the cooling and heating may be effected in a short time, thus shortening the time required for measuring. Further, the difference in temperature between the specimens is reduced, and therefore the fluctuation of results can be further reduced.

For the preparation of the solid phase which will be specifically combined with the substance to be measured, for use in this invention, it may be obtained by fixing another material which will be specifically combined with the measurable substance to an insoluble carrier. Examples of the material for such a carrier include polystyrene, cellulose, agarose, glass, crosslinked dextran, silicone rubber, metal etc. And, as its shape, a tube, a microtiter plate, cup, powder, sphere, disc, plate, flake etc. may be contemplated. For example, where polystyrene microtiter plate is employed as the carrier for making the antibody in the solid phase, the antibody is diluted appropriate with buffer etc., the diluted solution is added to the plate, followed by allowiing to stand, thereby the antibody is fixed to the inner wall of the plate and the antibody made in the solid phase is thus obtained.

As the enzyme to be used for the preparation of an enzyme-labelled product of the material which will be specifically combined with the substance to be measured, there may be mentioned the enzymes which are conveniently employed in enzyme immunoassay. For instance, illustrative enzymes include alkali phosphatase, peroxidase, $\beta$-D-galactosidase, glucoamylase, glucose oxidase etc. And as the method for labelling the enzyme, there may be employed the glutaraldehyde method, Nakane method, the maleimide method, the mixed acid anhydride method, the carbodiimide method etc. For example, the enzyme is added to the antibody, glutaraldehyde is added thereto to a concentration of 0.2-0.8%, and the reaction is effected at room temperature, thereby the enzyme-labelled product of the antibody is obtained.

As the substrate, there is used a substrate for the enzyme employed in the preparation of the enzyme-labelled product. Where the enzyme is alkali phosphatase, the substrate used may be p-nitrophenyl phosphate, $\beta$-glycerol phosphate, phenyl phosphate, $\beta$-naphthyl phosphate, phenolphthalein phosphate etc.

The solution for stopping the enzyme reaction used may be the known solution for each enzyme. In the case of alkali phosphatase, 1N sodium hydroxide is suitable.

The method of this invention has been described above, from which it will be understood that the substance which may be measured by the method of this invention is a substance which has a combination partner which will be specifically combined therewith. Examples of such a substance are those pair substance having the relatinship: antigen-antibody, and hapten-antibody. For example, there may be mentioned cancer related antigens such as $\alpha$-fetoprotein, CEA, BFP (NEA), aldolase, etc., hepatitis related antigens such as HB antigens (HBs, HBc, and HBe), HA antigen, non-A, non-B antigen etc., hormones such as insulin, HCG, immunoglobin, albumin, $\alpha$-macroglobulin, as well as their antibodies, etc.

For practicing this invention, there is used, for controlling the temperature, a test vessel which can be very readily and rapidly adjusted to the same intended temperature all over the vessel.

The above vessel comprises contacting and unifying, to a receiver made of a synthetic resin providing at least one concave portion, a base frame consisting of a thin layer plate or a foil which comprises a metal as a predominant component, the metal being capable of closely contacting to the outer wall of the receiver.

By employing such vessel, it can be readily controlled to a predetermined temperature, resulting in that the temperature difference between the specimens is reduced, and the reaction for the respective vessels may simultaneously proceed, whereby the fluctuation of the result can be reduced. In addition, the cooling and heating may be effected in a short time, thus shortening the time required for measuring.

As for a material which will be specifically combined with a partner substance to be measured and which has been made in a form of the solid phase, it can be obtained by fixing the material which will be specifically combined with the partner substance to be measured, with an insoluble carrier.

According to this invention, a receiver having at least one concave portion is shaped with a synthetic resin such as polystyrene, polyvinyl chloride, polyethylene, epoxy resin, and the like. The receiver functions as a reactor and as a material which will be specifically combined with the partner substance to be measured.

A base frame for intimately covering the outer wall of the receiver is fabricated with a thin layer plate or foil which comprises as a predominant component a good thermo-conductive metal such as aluminium, copper, iron, etc. The frame is then unified to the receiver. The frame has a function for rapidly conducting, to the receiver, a controlled reaction temperature through the cooling means and heating means.

The base frame is unified by evaporation, or thermal melting, or adhering by means of an ultrasonic waves, or an adhesive, etc. to the receiver.

FIG. 1 shows a sectional view of a test vessel comprising a receiver 1 and a frame 2, wherein the base or the bottom is a hemispheric shape 3.

FIG. 2 shows a sectional view of a test vessel comprising a receiver 1 and a frame 2, wherein the base is a flat shape 3, which is convenient to place the same on a metal plate of a cooling means or a heating means.

For example, when the receiver of this invention is placed on a cooling plate or on ice, the frame made of a good thermo-conductive metal is at once cooled, resulting in that the temperature is lowered, and the receiver made of a synthetic resin closely attached to the frame is cooled. The thermal conductivity to the receiver has a rapid cooling effect in both a direct method for directly cooling, and an indirect method which comprises cooling by inserting it into a thermostat, and the like.

The same effect is achieved in a heating procedure, of course.

FIG. 5 shows the comparison of the data of the sample, when the test vessel and the conventional vessel are respectively used.

Figure 1:
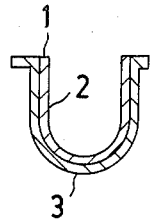
Figure 2:
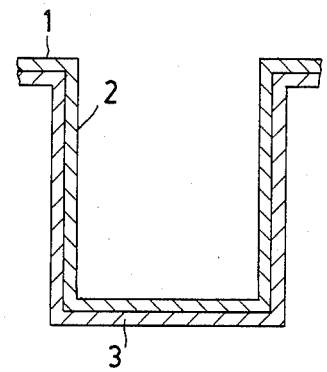

This invention is more particularly described by the following examples.

EXAMPLE 1

Measurement of α-Fetoprotein (a) Antihuman α-Fetoprotein Antibody Coated Cups:

To each polystyrene cup (6.5 mm in inner diameter and 10 mm in depth) was added 150 μl of a 0.5M tris-hydrochloric acid buffer (pH 8.0) containing 10 μg/ml of a purified antihuman α-fetoprotein antibody (rabbit), and this was allowed to stand at 4° C. overnight. The liquor portion was removed from each cup, which was then washed with distilled water, whereby the solid phased antihuman α-fetoprotein antibody cups had been obtained.

(b) Alkali Phosphatase-labelled Antihuman α-Fetoprotein Antibody:

To one ml of an alkali phosphatase solution (containing 3 mg of protein and 1000 units per mg of specific activity) was added 0.5 ml of a 0.05M tris-hydrochloric acid buffer containing 3 mg of a purified antihuman α-fetoprotein antibody. To the resulting mixed solution was added a 25% aqueous glutaraldehyde solution to adjust the glutaraldehyde concentration to 0.2%. The mixture was allowed to stand at room temperature for 3 hours. Thereafter, this was dialyzed against a 0.05M tris-hydrochloric acid buffer (pH 8.0) overnight, to obtain an alkali phosphatase-labelled antihuman α-fetoprotein antibody.

(c) Enzyme Immunoassay:

Measuring System A

The cups obtained in (a) above were inserted into the respective holes on an aluminum plate (aluminum holder) having 96 such holes (8 holes across × 12 holes lengthwise).

(1) This aluminum holder was placed on ice cubes, and under the cooling condition 100 μl portions of α-fetroprotein positive human serum (the α-fetroprotein concentration of 120 ng/ml and the temperature of the specimens of 19° C.) was added to the respective cups Nos. 1–48; 100 μl portions of the α-fetoprotein standard specimen (for preparing a calibration curve) to the respective cups Nos. 49–56; and 100 μl portions of the above α-fetoprotein positive human serum to the remaining respective cups Nos. 57–96, successively in the numerical order and using micropipettes.

(2) The aluminum holder was dipped in warm water at 37° C., and the reaction was effected for 60 minutes.

(3) The aluminum holder was taken out from the warm water and the respective internal liquors were successively removed by suction using an aspirator, after which each cup was washed with distilled water (i.e. by adding distilled water and removing it by suction) three times.

(4) The aluminum holder was placed on ice cubes. To the respective cups were respectively added 100 μl portions (4° C.) of a 400-fold dilution of the alkali phosphatase-labelled antihuman α-fetoprotein antibody obtained in the above (b) with 50% rabbit serum.

(5) The aluminum holder was dipped in warm water at 37° C., and the reaction was effected for 60 minutes.

(6) Similarly as in (3) above the removal of the cup internal liquor and washing were conducted.

(7) The aluminum holder was placed on ice cubes, and 100 μl portions (4° C.) of an aqueous p-nitrophenyl phosphate solution (4 mg/ml) were successively added to the respective cups.

(8) The aluminium holder was again dipped in warm water of 37° C., and the reaction was effected for 60 minutes.

(9) The aluminum holder was taken out from the warm water and placed on ice cubes to cool for 2 minutes, after which 100 μl portions (4° C.) for a 1N sodium hydroxide were successively added to the respective cups.

(10) The internal liquor of each cup was diluted with distilled water 11 times, and the optical density (OD) of each liquor was measured on a spectrophotometer at 405 mμ.

A calibration curve was prepared from the $OD_{405\ m\mu}$ of the cups Nos. 49–56, and the α-fetoprotein concentrations of Nos. 1–48 and Nos. 57–96 were obtained.

Measuring System B

In (3) and (6) of the Measuring System A, the aluminum holder taken out from the warm water was placed on ice cubes for 2 minutes to cool, and thereafter the remaining respective operations were carried out.

Measuring System C

In (4), (7) and (9) of the Measuring System A, the respective operations were carried out at room temperature (19° C.), without cooling the aluminum holder with ice cubes.

Measuring System D

In (1), (4), (7) and (9) of the Measuring System A, the respective operations were carried out at room temperature (19° C.), without cooling the aluminium holder with ice cubes.

The results of the measurements of α-fetoprotein by the Measuring Systems A–D are given in Table 1.

TABLE 1

| Specimen | Average Value ng/ml | | | | Coefficient of Variation (c.v.) % | | | |
|---|---|---|---|---|---|---|---|---|
| (Cup No.) | A | B | C | D (Control) | A | B | C | D (Control) |
| 1~16 | 122.8 | 108.8 | 117.1 | 142.6 | 4.9 | 1.9 | 9.0 | 8.4 |
| 17~32 | 124.3 | 114.9 | 111.3 | 127.1 | 4.1 | 4.2 | 6.1 | 7.3 |
| 33~48 | 128.7 | 114.7 | 112.6 | 116.7 | 2.4 | 7.0 | 5.6 | 6.5 |
| 57~64 | 131.8 | 115.6 | 109.1 | 113.9 | 1.6 | 3.8 | 4.7 | 6.2 |
| 65~80 | 124.4 | 116.7 | 109.9 | 112.8 | 4.6 | 2.6 | 4.0 | 6.3 |
| 81~96 | 120.3 | 116.4 | 109.7 | 96.8 | 3.7 | 3.1 | 4.8 | 7.1 |
| Total Specimens (Nos. 1-48, & 57-96) | 124.8 | 114.4 | 111.8 | 117.6 | 4.6 | 4.7 | 6.4 | 17.5 |

As shown in the table, in the Measuring System D (control) where no cooling operation was conducted, the fluctuation in measured values is very broad. In other words, the coefficient of variation for the total specimens ranges as broad as 17.5%. In addition, the average value for Nos. 1-16 amounts to 142.6 ng/ml, while the average value for Nos. 81-96 amounts to 96.8 ng/ml. That is, there is a disadvantage that the results are greatly different from one another depending on the order in the measuring operation.

On the contrary, in the Measuring System A, B and C where the cooling operation was conducted in accordance with this invention, there is achieved a characteristic advantage that the fluctuation of results is very narrow.

EXAMPLE 2

Measurement of α-Fetoprotein

Using the Measuring System A in Example 1, α-fetoprotein positive human serum (the α-fetoprotein concentration of 120 ng/ml and the temperature of the specimens of 4° C.) was measured. As the control, the measurements were conducted using the Measuring System D in Example 1. The results are given in Table 2.

TABLE 2

| Specimen (Cup No.) | Average Value ng/ml | | Coefficient of Variation (c.v.) % | |
|---|---|---|---|---|
| | This Invention | Control | This Invention | Control |
| 1-16 | 115.3 | 142.9 | 2.5 | 11.3 |
| 17-32 | 124.1 | 131.2 | 3.5 | 4.5 |
| 33-48 | 113.3 | 125.9 | 3.4 | 3.3 |
| 57-64 | 122.3 | 124.6 | 3.2 | 3.8 |
| 65-80 | 115.8 | 117.0 | 5.3 | 2.8 |
| 81-96 | 119.6 | 113.9 | 3.6 | 4.1 |
| Total Specimens (Nos. 1-48 & 57-96) | 118.0 | 126.1 | 4.9 | 10.1 |

As shown in the above table, also when conducting the measurement of the specimens which have been previously cooled to 4° C., the fluctuation of results and coefficient of variation are smaller, when the cooling operation according to this invention is additionally conducted.

EXAMPLE 3

Measurement of α-Fetoprotein:

The measurement of α-fetoprotein positive human serum (the α-fetoprotein concentration of 130 ng/ml and the temperature of the specimens of 28° C.) was conducted according to the Measuring System A in Example 1. For assays of the specimens, cups Nos. 1-96 were used. The assay of the standard specimen was conducted with separately prepared cups at the time between the assays of the cups Nos. 48 and 49. The room temperature was 28° C. Instead of cooling with ice cubes in (1), (4), (7) and (9) in the Measuring System A in Example 1, cooling was effected using water of 3° C., 7° C., 10° C. and 15° C., respectively. For the controls, the operations were conducted at room temperature (28° C.) and with cooling using cold water of 20° C. in these (1), (4), (7) and (9). The results are given in Table 3.

TABLE 3

| Cooling Temperature | Specimen No. 1 ng/ml | Specimen No. 96 ng/ml | Average Value (Nos. 1-96) ng/ml | Coefficient of Variation (c.v.) (Nos. 1-96)% |
|---|---|---|---|---|
| 28° C. (control) | 225 | 95 | 129 | 24.9 |
| 20° C. (Control) | 171 | 111 | 127 | 15.8 |
| 15° C. | 150 | 116 | 128 | 11.5 |
| 10° C. | 137 | 127 | 132 | 8.7 |
| 7° C. | 138 | 129 | 128 | 7.2 |
| 3° C. | 141 | 140 | 131 | 6.0 |

As shown in the table, the lower the cooling temperature, the smaller the fluctuation of results and coefficient of variation.

EXAMPLE 4

Measurement of Human Muscle Type Aldolase (a) Antihuman Muscle Type Aldolase Antibody Coated Cups:

Using a purified antihuman muscle type aldolase antibody (chicken), procedures similar to those in (a) in Example 1 were conducted to obtain cups to which the antihuman muscle type aldolase antibody had been combined.

(b) Alkali Phosphatase-labelled Antihuman α-Fetoprotein Antibody:

Using the purified antihuman muscle type aldolase antibody (chicken), procedures similar to those in (b) in Example 1 were conducted to obtain an alkali phosphatase-labelled antihuman α-fetoprotein antibody.

(c) Enzyme Immunoassay:

Into the aluminum holder employed in Example 1 were inserted 54 cups obtained in (a) above. This aluminum holder was placed on ice cubes and under cooling condition 100 μl portions of human muscle type aldolase positive human serum (the human muscle type aldolase concentration of 250 ng/ml and the temperature of the specimens of 19° C.) were added to the respective cups Nos. 1-24; 100 μl portions of the human muscle type aldolase standard specimen (for preparing a calibration curve) to the respective cups Nos. 25–32; and 100 μl portions of the above human muscle type aldolase positive human serum to the respective cups Nos. 33–56, successively in the numerical order. The aluminum holder was dipped in warm water at 37° C., and the reaction was effected for 60 minutes. The aluminum holder was taken out from the warm water, and the internal liquor of each cup was removed by suction using an aspirator, and washed with distilled water (i.e. adding distilled water and removing it by suction) three times. At room temperature (19° C.), 100 μl portions (4° C.) of a 400-fold dilution of the alkali phosphatase-labelled antihuman muscle type aldolase antibody obtained in the above (b) with 50% rabbit serum were successively added to the respective cups. The aluminum holder was dipped in warm water at 37° C., and the reaction was effected for 60 minutes. The aluminum holder was then taken out from the warm water, and after removing each cup's internal liquor by suction, the cup was washed with distilled water three times similarly as the above. At room temperature, 100 μl portions (4° C.) of an aqueous p-nitrophenyl phosphate solution (4 mg/ml) were successively added to the respective cups. The aluminum holder was dipped in warm water at 37° C., and the reaction was effected for 60 minutes. The aluminum holder was taken out from the warm water, and 100 μl portions (4° C.) of a 1N sodium hydroxide were successively added to the respective cups. The internal liquor of each cup was diluted 11 times with distilled water, and the optical density was measured on a spectorphotometer at 405 mμ. A calibration curve was prepared, from which the concentration of the human muscle type aldolase in each specimen was determined. The results are given in the following table.

TABLE 4

| Specimen (Cup No.) | Average Value ng/ml | Coefficient of Variation (C.V.) % |
|---|---|---|
| 1–16 | 260.4 | 5.7 |
| 17–24, 33–40 | 253.1 | 5.1 |
| 41–56 | 248.9 | 5.5 |
| Total Specimen (Nos. 1–24 & 33–56) | 254.0 | 5.6 |

EXAMPLE 5

Measurement of HBs Antigen (a) Anti-HBs Antibody Coated Cups:

Using a purified anti-HBs antibody (rabbit), procedures similar to those in (a) in Example 1 were conducted to obtain cups to which the anti-HBs antibody had been combined.

(b) Alkali Phosphatase-labelled Anti-HBs Antibody:

Using the purified anti-HBs antibody (rabbit), procedures similar to those in (b) in Example 1 were conducted to obtain an alkali phosphatase-labelled anti-HBs antibody.

(c) Enzyme Immunoassay:

Into the aluminum holder employed in Example 1 were inserted 18 cups obtained in the above (a). This aluminum holder was placed on ice cubes, and under cooling condition 100 μl portions of HBs antigen positive human serum (the HBs antigen concentration of 210 ng/ml and the temperature of the specimens of 19° C.) were added to the respective cups Nos. 1–6, 100 μl portions of the HBs antigen standard specimen (for preparing a calibration curve) to the respective cups Nos. 7–12, and 100 μl portions of the above HBs antigen positive human serum to the respective cups Nos. 13–18, successively in the numerical order. The aluminum holder was dipped in warm water at 37° C., and the reaction was effected for 60 minutes. The aluminum holder was then taken out from the warm water, and the contents of the cups were removed successively by suction using an aspirator, and washed with distilled water (i.e. adding distilled water and removing it by suction) three times. At room temperature (19° C.), 100 μl portions (4° C.) of a 400-fold dilution of the alkali phosphatase-labelled anti-HBs antibody obtained in the above (b) with 50% rabbit serum were successively added to the respective cups. Thereafter, similar procedures as those in Example 4 were conducted, to measure the HBs antigen in the specimens. The average value of the total specimens (No. 1–6 and 13–18) amounted to 211.1 ng/ml and the coefficient of variation (c.v.) amounted to 4.2%.

EXAMPLE 6

Figure 3:
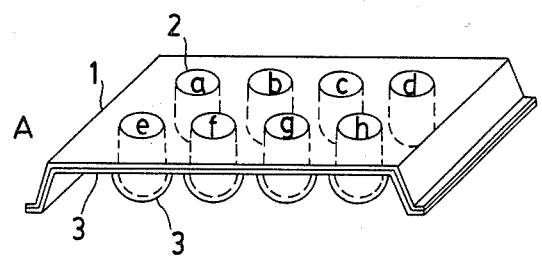
FIG. 3 shows a test vessel of this invention, wherein a plurality of concave portions are provided.

With reference to FIG. 3, a receiver 1 made of synthetic resin is prepared by providing concave portions 2 such as eight cup-like concaves a, b, c, d, e, f, g and h, each having an inner diameter of 8 mm and a depth of 10 mm.

The frame 3 which was prepared by casting an aluminium plate is closely contacted to the outer wall of the receiver 1, in order to prepare a test vessel A. To the respective concaves were added 100 μl portions of α-fetoprotein positive human serum (the α-fetoprotein concentration of 120 ng/ml). The subsequent procedures are carried out in accordance with the description in Example 1, Measuring System A. And, the optical density (OD) was measured on a spectrophotometer at 405 mμ.

Figure 4:
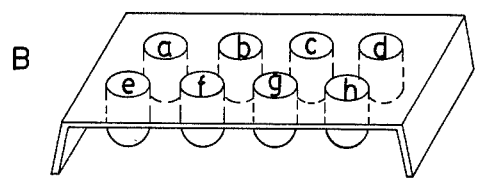
FIG. 4 shows a conventional vessel made of synthetic resin, wherein a plurality of concave portions are provided, and the frame is not contacted.

Conventional vessel B is used as shown in FIG. 4, wherein the frame is not contacted.

FIG. 5 shows the data of the optical densities for the sample by the use of the test vessel A of this invention and the conventional vessel B. It is apparent that the data by the test vessel A has less fluctuation than those by the conventional vessel B. There is also obtained an advantageous merit that the mean values of the optical densities of the former are higher than those of the latter, such as above 10%.

What is claimed is:

1. In a method for simultaneously assaying a plurality of specimens for a given substance by enzyme immunoassay which comprises the steps of:

(a) reacting a plurality of specimens of a substance to be assayed with a solid phase material which is capable of being immunochemically specifically reacted with the substance to be assayed in said specimens;

(b) separating the reaction mixture in the step (a) into a solid phase and a liquid phase;

(c) reacting the solid phase of step (b) with an enzyme-labelled product of a material which is capable of being immunochemically specifically reacted with the substance to be assayed;

(d) separating the reaction mixture in the step (c) into a solid phase and a liquid phase;

(e) reacting the solid phase or the liquid phase of step (d) with a substrate for the enzyme in the step (c); and (f) measuring the optical density of the reaction mixture of step (e);

wherein the improvement comprises in step (a), the respective specimens are successively contacted with said solid phase material, under cooling conditions at a temperature ranging from 0° C. to 15° C., followed by incubating all the specimens simultaneously at a temperature ranging from room temperature to 45° C., prior to step (b).

2. The method of claim 1 wherein the solid phase comprises an insoluble carrier placed in a vessel.

3. The method of claim 1 wherein the successive addition of the enzyme-labelled product to the solid phase in step (c) is effected at a temperature ranging from 0° C. to 15° C., and the reaction is then conducted at a temperature ranging from room temperature to 45° C.

* * * * *